United States Patent [19]

Halmos

[11] 4,151,198

[45] Apr. 24, 1979

[54] RESOLUTION OF N-ACYL-DL(+)-PHENYLALANINES

[75] Inventor: Imre A. Halmos, Summit, N.J.

[73] Assignee: American Cyanamid Company, Stamford, Conn.

[21] Appl. No.: 911,841

[22] Filed: Jun. 2, 1978

[51] Int. Cl.$^2$ ............................................. C07C 101/08
[52] U.S. Cl. ................................. 260/501.11; 562/401
[58] Field of Search ..................... 260/501.11; 562/401

[56] References Cited

U.S. PATENT DOCUMENTS

| | | | |
|---|---|---|---|
| 3,734,952 | 5/1973 | Krubiner | 562/401 |
| 3,969,397 | 7/1976 | Kaiser et al. | 562/401 |
| 4,005,088 | 1/1977 | Gubbels et al. | 562/401 |
| 4,016,205 | 4/1977 | Kariyone et al. | 562/401 |

*Primary Examiner*—Bernard Helfin
*Assistant Examiner*—James H. Reamer
*Attorney, Agent, or Firm*—Charles F. Costello, Jr.

[57] ABSTRACT

The treatment of N-acyl-DL(+)-phenylalanines with D(−)-2-(2,5-dimethylbenzylamino)-1-butanol results in the formation of the D(−)-2-(2,5-dimethylbenzylamino)-1-butanol salt which is obtained as a crystallizate of the N-acyl-L(+)-phenylalanine and from which the desired N-acyl-L(+)-phenylalanine, an intermediate useful for the preparation of artificial sweetening agents, can be recovered.

6 Claims, No Drawings

RESOLUTION OF N-ACYL-DL (+)-PHENYLALANINES

BACKGROUND AND SUMMARY OF THE INVENTION

This invention relates to a process for the resolution of N-acyl-DL(±)-phenylalanines to obtain N-acyl-L(+)-phenylalanines which can be hydrolyzed to obtain L(−)-phenylalanine, an intermediate useful in the manufacture of methyl α-L-aspartyl-L-phenylalanate, a sweetening agent disclosed by Anderson in U.S. Pat. No. 3,901,871.

Heretofore it has been difficult to obtain N-acyl-L(+)-phenylalanines by either asymmetric synthesis or the resolution of N-acyl-DL(±)-phenylalanines. Prior art methods have employed optically active amines. However, since none of the optically active amines has been found to be completely satisfactory, research continues in order to find new optically active amines which will be more satisfactory. The present invention arose out of such research and resulted in the discovery of a more economical and facile process for the resolution of N-acyl-DL(±)-phenylalanines.

In accordance with the present invention, there is provided a process for resolving N-acyl-DL(±)-phenylalanines represented by formula (I)

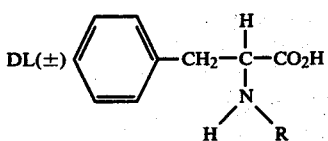

wherein R represents an acyl radical selected from $C_1$-$C_8$ alkanoyl, or benzoyl, comprising:

(a) reacting about one mole of said compound of formula (I) with about one mole of D(−)-2-(2,5-dimethylbenzylamino)-1-butanol, represented by formula (II)

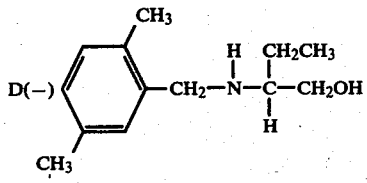

in an aqueous medium at moderately elevated temperatures to form an essentially saturated solution of a compound represented by formula (III)

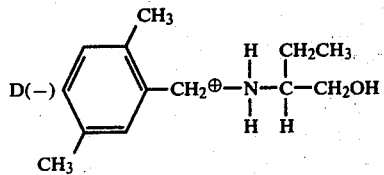

wherein R is as previously defined, (b) cooling said essentially saturated solution to crystallize said compound of formula (III) and recovering the same, (c) reacting said compound of formula (III) in an aqueous medium with an acid or alkalizing agent to form an optically pure N-acyl-L(+)-phenylalanine represented by formula (IV)

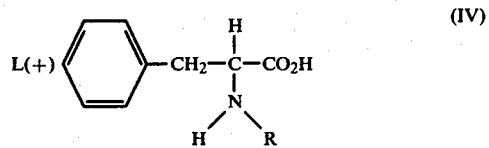

and recovering the same.

The preferred compound of formula (I) is N-acetyl-DL(±)phenylalanine.

In accordance with the present invention, there is also provided an alternative process for resolving compounds represented by formula (I) which comprises:

(a) reacting about one mole of said compound of formula (I) with about 0.5 mole of said compound of formula (II) and about 0.5 mole of an alkalizing agent in an aqueous medium at moderately elevated temperatures to form said essentially saturated solution of said compound of formula (III), and following steps (b) and (c) above to recover N-acyl-L(+)-phenylalanine therefrom. The preferred compound of formula (I) is N-acetyl-DL(±)-phenylalanine.

In accordance with the present invention, there are also provided novel compositions of matter represented by formula (III). The preferred species of formula (III) is wherein R is acetyl.

The processes of this invention are advantageous in that the resulting N-acyl-L(+)-phenylanilines are obtained in high yields and very high optical purity, without complicated isolation or recrystallization procedures, for subsequent conversion to the desired L(−)-phenylalanine.

DESCRIPTION OF THE INVENTION

Optically active isomers rotate the plane of polarized light either to the right or to the left. The dextrorotatory form is indicated by the prefixes d or (+), while the levorotatory form is indicated by the prefixes l or (−). If the two forms are present in equal amounts, the unresolved mixture is called racemic, dl, or (±).

Some optical isomers are also distinguished by the prefixes D or L. These symbols are used where the molecular configuration is known, often through synthesis from another molecule of established configuration. The optical rotation is then indicated by the additional symbol, (+) or (−), as described above.

As used herein, the term "acyl" is defined as a radical obtained by the removal of a hydroxy group from a $C_1$-$C_8$ aliphatic carboxylic acid or benzoic acid.

The compounds of formula (I) can be prepared by known procedures for acylation of DL(±)-phenylalanine by the Schotten-Baumann reaction involving treating the DL(±)-phenylalanine with an acyl chloride in caustic solution, or by treating the DL(±)-phenylalanine in acetic acid with acetic anhydride at elevated temperatures (see Town, U.S. Pat. No. 2,867,654).

Illustrative examples of the racemates of formula (I) include:
N-formyl-DL(±)-phenylalanine,
N-acetyl-DL(±)-phenylalanine, N-propionyl-DL(±)-phenylalanine,
N-n-butryl-DL(±)-phenylalanine, N-n-caproyl-DL(±)-phenylalanine,
N-n-octanoly-DL(±)-phenylalanine, and
N-benzoyl-DL(±)-phenylalanine, and the like.

D(−)-2-(2,5-Dimethylbenzylamino)-1-butanol can be prepared by reacting 2,5-dimethylbenzyl chloride with excess D(−)-2-amino-1-butanol. The preparation of D(−)-2-amino-1-butanol is described in Beilstein 4, 291.

The process of this invention is carried out by reacting about one mole of D(−)-2-(2,5-dimethylbenzylamino)-1-butanol per mole of a compound of formula (I), preferably N-acetyl-DL(±)-phenylalanine, in an aqueous medium at a moderately elevated temperature of about 50°–90° C., preferably about 70°–80° C., sufficient amounts of reactants and aqueous medium being used to provide an essentially saturated solution of a compound of formula (III), gradually cooling the reaction mixture to about 15° to 25° C., preferably about 20° C., and recovering the yield therefrom. Preferably, the saturated solution is seeded with a small amount of the compound of formula (III), before cooling, in order to promote the crystallization of the compound of formula (III).

The compound of formula (III) is converted to its components by acidifying or alkalizing in water at about 30° to 35° C. to form a slurry of the compound of formula (III) or formula (II), respectively.

Suitable acids for the acidification of the compound of formula (III) include acetic, formic, propionic, aqueous hydrochloric and the like. The preferred acid is acetic acid.

Any alkalizing agent capable of effecting the precipitation of the compound of formula (II) is suitable for the purpose of this invention. Preferred alkalizing agents are sodium hydroxide and potassium hydroxide.

If acidification is carried out first the compound of formula (IV) is separated and the compound of formula (II) is recovered by alkalizing the mother liquor. If alkalizing is carried out first the compound of formula (II) is separated and the compound of formula (IV) is recovered by acidifying the mother liquor.

The number of equivalents of acid or base used is slightly in excess of the number of moles of the compound of formula (III).

Deacylation of the compound of formula (IV) can be effected at elevated temperatures with aqueous hydrochloric acid in accordance with known procedures to obtain L(−)-phenylalanine.

The D(−) enantiomorphs of the compounds of formulas (III) and (IV) remain in solution after the separation of the compound of formula (III). These can be recovered by slightly acidifying the mother liquors and cooling to effect crystallization. The D(−) enantiomorph of formula (IV) can be converted with base to a racemic mixture of formula (I) which can be reacylated and recycled.

Examples of compounds of formula (III) which fall within the purview of this invention include the D(−)-2-(2,5-dimethylbenzylamino)-1-butanol salts of
N-formyl-L(+)-phenylalanine,
N-acetyl-L(+)-phenylalanine,
N-propionyl-L(+)-phenylalanine,
N-n-butyryl-L(+)-phenylalanine,
N-n-caproyl-L(+)-phenylalanine,
N-n-octanoyl-L(+)-phenylalanine,
N-benzoyl-L(+)-phenylalanine, and the like.

In the alternate process about one-half mole of D(−)-2-(2,5-dimethylbenzylamino)-1-butanol and about one-half equivalent of an alkalizing agent are reacted per mole of N-acyl-DL(+)-phenylalanine used in step (a). The preferred compound of formula (I) is N-acetyl-DL(+)-phenylalanine.

Alkalizing agents suitable for use in the alternate process include sodium hydroxide, potassium hydroxide, ammonium hydroxide, and water soluble organic amines such as ethylamine, dieethylamine, diisopropylamine, triethylamine, ethanolamine, diethanolamine, and the like.

The following examples further illustrate the invention. Optical rotations were measured by dissolving the indicated concentration of the compound in grams in 100 mls of solvent and determining the rotation of the plane of the sodium D line at 25° C.

EXAMPLE 1

D(−)-2-(2,5-Dimethylbenzylamino)-1-Butanol 2,5-Dimethylbenzyl chloride (78.4 grams; 0.50 mole) was added to D(−)-2-amino-1-butanol (160.0 grams; 1.79 moles) at 65°–72° C. over a period of about 30 minutes while stirring the reaction mixture. The reaction mixture was −stirred at 85°–90° C. for one hour, cooled to about 45° C., and poured into 500 mls of water. The resulting slurry was made alkaline to pH 11 by adding 50% caustic soda thereto and filtered. The filter cake was washed with water and recrystallized from 200 mls of acetone to obtain 83.5 grams (79.5% of theoretical) of D(−)-2-(2,5-dimethylbenzylamino)-1-butanol, m.p. 85°–88° C., $[\alpha]D^{25} = -28.0°$ (C, 2.5; methanol).

EXAMPLE 2

N-Acetyl-DL(±)-Phenylalanine

To a stirred mixture of 100.0 grams of DL(±)-phenylalanine in 600 grams of water at 10°–20° C. is added, portionwise, an aqueous solution of 50% sodium hydroxide to adjust the solution to pH 12. Then, 185 grams of acetic anhydride are added, slowly while simultaneously adding 50% aqueous sodium hydroxide to maintain the reaction mixture at pH 12 and cooling the mixture to maintain the temperature between 10°–30° C. After about 20 minutes, the reaction mixture is acidified to pH 1 with concentrated hydrochloric acid and filtered. The recovered solid is recrystallized from water and ethanol to obtain N-acetyl-DL(±)-phenylalanine, m.p. 148° C.

In the manner described above substituting equivalent amounts of benzoyl chloride, n-butyric anhydride, and n-caproyl chloride for the acetic anhydride N-benzoyl-DL(±)-phenylalanine, N-n-butyryl-DL(±)-phenylalanine, and N-n-caproyl-DL(±)-phenylalanine, respectively, are obtained.

EXAMPLE 3

D(−)-2-(2,5-Dimethylbenzylamino)-1-Butanol Salt of N-Acetyl-L(+)-Phenylalanine

N-Acetyl-DL(±)-phenylalanine (30.0 grams; 0.145 mole) and D(−)-2-(2,5-dimethylbenzylamino)-1-butanol (30.0 grams; 0.145 mole) were dissolved in 300 mls of water at 80° C. and the solution was gradually cooled to 40° C. to form a heavy, crystalline slurry. The slurry was cooled to 20° C., and filtered; the filter cake was washed with 50 mls of ice cold (5° C.) water and dried to obtain 21.7 grams (72.3% of theoretical) of the D(−)-2-(2,5-dimethylbenzylamino)-1-butanol salt of N-acetyl-L(+)-phenylalanine.

Following the above procedure substituting equivalent amounts of N-benzoyl-DL(±)-phenylalanine, N-n-butyryl-DL(±)-phenylalanine, and N-n-caproyl-DL(±)-phenylalanine for the N-acetyl-DL(±)-phenylalanine the D(−)-2-(2,5-dimethylbenzylamino)-1-butanol salts of N-benzoyl-L(+)-phenylalanine, N-n-butyryl-L(+)-phenylalanine, and N-n-caproyl-L(+)-phenylalanine, respectively, are obtained.

EXAMPLE 4

N-Acetyl-L(+)-Phenylalanine

The D(−)-2-(2,5-dimethylbenzylamino)-1-butanol salt of N-acetyl-L(+)-phenylalanine (10.0 grams; 0.024 mole) from Example 3 was slurried in 40 mls of water at 30°–35° C. and acidified with acetic acid to obtain a weak blue spot on Congo Red indicator paper. The resulting slurry was cooled to 5° C. and filtered. The resulting filter cake was washed with ice cold water and dried to obtain 4.5 grams (90% of theoretical) of N-acetyl-L(+)-phenylalanine, m.p. 168.5°–169.8° C., $[\alpha]_D^{25}$ = 50° (C = 1; ethanol).

In the manner described above utilizing equivalent amounts of the other products obtained in Example 3 N-benzoyl-L(+)-phenylalanine, N-n-butyryl-L(+)-phenylalanine, and N-n-caproyl-L(+)-phenylalanine are obtained.

EXAMPLE 5

Alternate Preparation of D(−)-2-(2,5-Dimethylbenzylamino)-1-Butanol Salt of N-L(+)-Phenylalanine N-Acetyl-DL(±)-phenylalanine (50 grams; 0.24 mole) and D(−)-2-(2,5-dimethylbenzylamino)-1-butanol (25.0 grams; 0.12 mole) were slurried in 100 mls of water and 120 mls of one molar aqueous sodium hydroxide (0.12 mole) was slowly added thereto while raising the temperature to about 45° C. The reaction mixture was cooled to crystallize the product at about 38° C. and then stirred at about 10° C. for 3 hours. The crystals were then filtered, washed with cold water and dried to obtain 32.0 grams of the D(−)-2-(2,5-dimethylbenzylamino)-1-butanol salt of N-acetyl-L(+)-phenylalanine.

The addition of 25 grams of sodium sulfate to the mother liquors plus wash water resulted in the recovery of 10.3 grams of a second crop of product. The total yield in two crops was 84.6% of theoretical.

EXAMPLE 6

Recovery of N-Acetyl-D(−)-Phenylalanine

The mother liquors obtained in Example 3 were treated with hydrochloric acid to produce a weak blue spot on Congo Red indicator paper (pH 4.5–5.0), cooled to 5° C. and allowed to stand for about 3 hours. The resulting precipitate was filtered, washed with ice cold water and dried to obtain 13.1 grams (87.3% of theoretical) of N-acetyl-D(−)-phenylalanine, m.p. 157°–161° C., $[\alpha]_D^{25}$ = −49.8° (C, 1.0; ethanol).

EXAMPLE 7

Recovery of D(−)-2-(2,5-Dimethylbenzylamino)-1-Butanol

The mother liquor and wash liquor obtained in Example 4 were combined and made alkaline by adding 50% caustic soda thereto. After standing at ambient conditions for several hours, the slurry was filtered, washed with water and dried to obtain 4.9 grams (98% of theoretical) of D(−)-2-(2,5-dimethylbenzylamino)-1-butanol.

I claim:

1. A process for resolving racemic N-acyl-DL(±)-phenylalanine represented by formula (I)

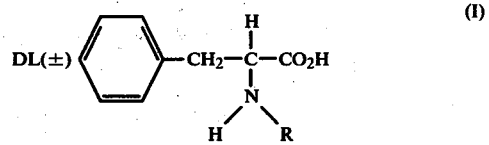

wherein R represents an acyl radical selected from $C_1$-$C_8$ alkanoyl, or benzoyl, comprising:
(a) reacting about one mole of said compound of formula (I) with about one mole of D(−)-2-(2,5-dimethylbenzylamino)-1-butanol, represented by formula (II),

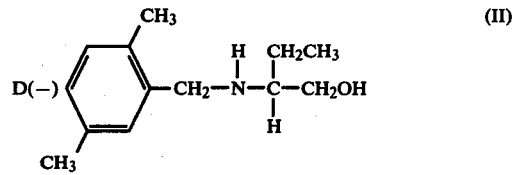

in an aqueous medium at a temperature of about 50°–90° C. to form an essentially saturated solution of a compound represented by formula (III)

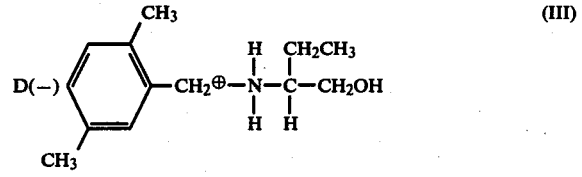

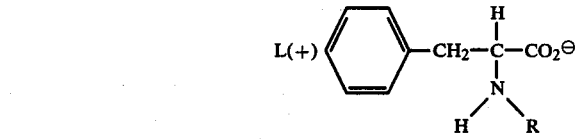

wherein R is as previously defined,
(b) cooling said essentially saturated solution to crystallize said compound of formula (III), and recovering the same,
(c) reacting said compound of formula (III) in an aqueous medium with an acid or alkalizing agent to form an optically pure N-acyl-L(+)-phenylalanine represented by formula (IV)

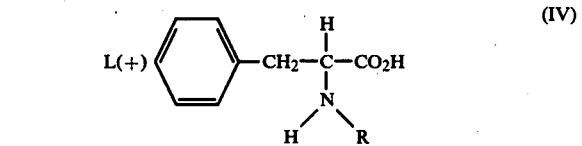

and recovering the same.

2. The process according to claim 1 wherein the compound of formula (I) is N-acetyl-DL(±)-phenylalanine.

3. A process according to claim 1 comprising:

(a) reacting about one mole of said compound of formula (I) with about 0.5 mole of said compound of formula (II) and about 0.5 mole of an alkalizing agent in an aqueous medium at a temperature of about 50°–90° C. to form said essentially saturated solution of said compound of formula (III), and following steps (b) and (c) of claim 1 to recover N-acyl-L(+)-phenylalanine therefrom.

4. The process according to claim 3 wherein the compound of formula (I) is N-acetyl-DL(±)-phenylalanine.

5. A composition of matter represented by formula

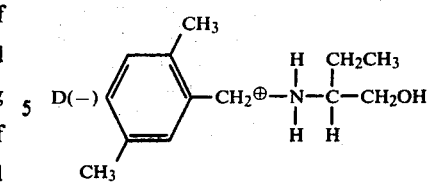

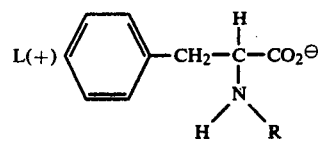

wherein R represents an acyl radical selected from $C_1$-$C_8$ alkanoyl, or benzoyl.

6. The composition of claim 5 wherein R is acetyl.

* * * * *